United States Patent [19]
Geisser et al.

[11] Patent Number: 5,454,815
[45] Date of Patent: Oct. 3, 1995

[54] BONE RASP MADE OF PLASTICS

[75] Inventors: Albert Geisser, Ennetburgen, Switzerland; Hubertus Becker, Apfeldorf, Germany; Heinz Elmiger, Malters, Switzerland

[73] Assignee: IMT Integral Medizintechnik Trading AG, Ennetburgen, Switzerland

[21] Appl. No.: 293,739

[22] Filed: Aug. 22, 1994

Related U.S. Application Data

[63] Continuation of Ser. No. 34,160, Mar. 22, 1993, abandoned.

[30] Foreign Application Priority Data

Apr. 1, 1992 [CH] Switzerland ............. 1043/92

[51] Int. Cl.[6] .................................. A61B 17/88
[52] U.S. Cl. .................................. 606/85; 606/79
[58] Field of Search ............... 606/85, 84, 82, 606/80, 81, 92, 95, 99, 100, 176, 177, 178, 179; 29/78, 79, 80; 132/76.4, 76.5; 408/227, 228, 229, 230, 231

[56] References Cited

U.S. PATENT DOCUMENTS

| | | | |
|---|---|---|---|
| D. 273,806 | 5/1984 | Bolesky et al. | D24/28 |
| 4,552,136 | 11/1985 | Kenna | 606/85 |
| 4,757,571 | 7/1988 | Young | 15/167.3 |
| 4,773,406 | 9/1988 | Spector et al. | 606/76 |
| 4,808,186 | 2/1989 | Smith | 623/23 |
| 5,006,121 | 4/1991 | Hafeli | 606/85 |
| 5,009,664 | 4/1991 | Sievers | 623/16 |
| 5,015,256 | 5/1991 | Bruce et al. | 623/18 |
| 5,100,267 | 3/1992 | Salyer | 407/54 |
| 5,124,106 | 6/1992 | Morr et al. | 264/221 |
| 5,169,401 | 12/1992 | Lester et al. | 606/79 |
| 5,176,155 | 1/1993 | Rudolph, Jr. | 132/76.4 |
| 5,269,785 | 12/1993 | Bonutti | 606/80 |

FOREIGN PATENT DOCUMENTS

| | | | |
|---|---|---|---|
| 136079 | 4/1985 | European Pat. Off. | |
| 253526 | 1/1988 | European Pat. Off. | |
| 296986 | 12/1988 | European Pat. Off. | 606/85 |
| 331622 | 9/1989 | European Pat. Off. | |
| 405132 | 1/1991 | European Pat. Off. | |
| 2274267 | 1/1976 | France | |
| 2503988 | 4/1981 | France | |
| 2503988 | 10/1982 | France | |
| 2547192 | 12/1984 | France | 606/85 |
| 2732325 | 1/1979 | Germany | 606/85 |
| 8601685 | 3/1986 | Germany | |
| 3907256 | 9/1990 | Germany | |
| 611509 | 6/1979 | Switzerland | |

OTHER PUBLICATIONS

"DePuy Hip Prosthesis" Journal of Bone and Joint Surgery, vol. 45-A #6, Sep. 1963, p. 61, (auther unknown).

*Primary Examiner*—Stephen C. Pellegrino
*Assistant Examiner*—Guy V. Tucker
*Attorney, Agent, or Firm*—Parmelee, Bollinger & Bramblett; George W. Rauchfuss, Jr.

[57] ABSTRACT

A bone rasp for the working of bones said rasp having a plastic toothed working section with teeth and cutting edges and a connecting section, optionally made of plastic, for connecting the rasp to an impact tool. This rasp can be manufactured inexpensively, making possible one-time use and thereby making cleaning and sterilization of the used rasp unnecessary.

11 Claims, 1 Drawing Sheet

BONE RASP MADE OF PLASTICS

This is a continuation of application Ser. No. 08/034,160 filed on Mar. 22, 1993, now abandoned.

BACKGROUND OF THE INVENTION

1. Field of the Invention

The invention relates to a rasp for the working of bones, the rasp comprising a toothed working part and a connecting part for the fixation of the rasp to an impact tool.

2. Description of the Prior Art

The bearing surfaces of bones which are to receive a prosthesis (for example an artificial hip joint) are worked on and are finished by rasps made of metal or metal alloys. Known are rasps made of steel, stainless steel, surface treated steel, chemically nickel-coated steel or chrome-plated steel, respectively. Such rasps are known in various shapes and sizes. The known rasps are cleaned and are sterilized in a sterilizer after each operation. These steps are not without problems for several reasons. After the operation the rasps are contaminated with blood and bone material and have to be cleaned manually e.g. with a brush. This is an unpleasant work and there is a considerable danger of injury of the worker due to the sharp cut or chiselled teeth of the rasp. On the other hand, there is a considerable risk that the rasps come into contact with each other or with other metal parts during cleaning and sterilization and that the rasps lose their sharpness by such contacts. The rasp's teeth are getting blunt of course as well by the repeated normal use of the rasps. Even a very small bluntness of the teeth, however, causes a considerable disadvantage (longer operation time, overheating and destroying of bone material). Furthermore the known rasps made of metal are heavy, making their manipulation during operation tiresome.

SUMMARY OF THE INVENTION

Hence, it is a general object of the invention to provide a bone rasp which overcomes the aforementioned drawbacks. It is thus an object of the invention to provide a rasp that avoids the cleaning and sterilizing steps and yet is always sterile and ready for operation. Another object is to provide a rasp that is always ready for operation in sharp as new condition. A yet another object is to provide a rasp that is light and therefore easy to handle by the surgeon. Yet another object of the invention is to provide a rasp that is easy to manufacture and inexpensive.

Now, in order to implement these and still further objects of the invention, which will become more readily apparent as the description proceeds, the bone rasp according to the invention is manifested by the feature that the working part of the rasp is made of plastics.

In a preferred embodiment of the rasp, the connecting part is made of plastics as well.

By such a rasp which is made at least partially (the working part) but preferably as a whole of plastic material, the aforementioned problems are overcome. With such a bone rasp, which can be manufactured inexpensively, the multiple use of the rasp can be avoided. The rasp will be discarded after a single use and has therefore neither to be cleaned nor sterilized. The rasp is new for each operation and it is therefore sharp. The rasp will preferably be sterilized after manufacturing and packed to keep it sterile until use thereof. The rasp made of plastic is very light making its handling during operation easy.

BRIEF DESCRIPTION OF THE DRAWINGS

The invention will be better understood and objects other than those set forth above will become apparent when consideration is given to the following detailed description thereof. Such description makes reference to the annexed drawings, wherein.

DESCRIPTION OF THE PREFERRED EMBODIMENTS

Figure 1:
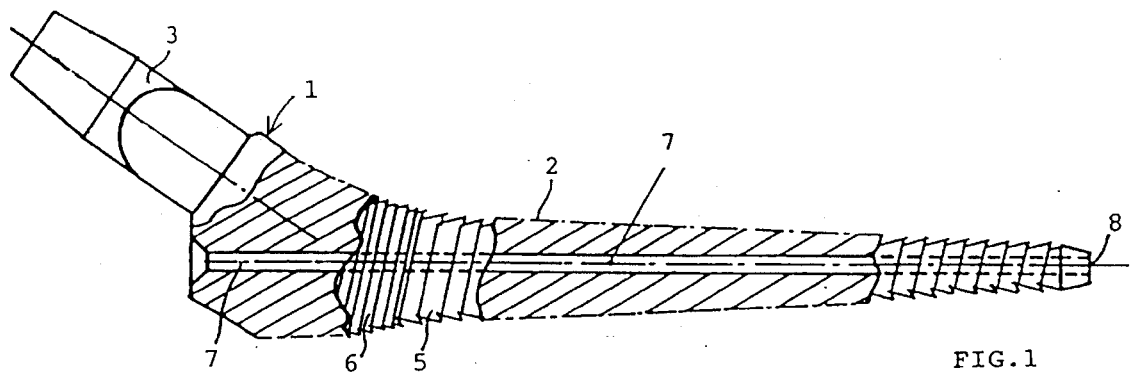
FIG. 1 is a (partly sectional) view of the broader side of a bone rasp according to the invention.

FIG. 1 shows the broadside of a bone rasp 1 made of plastic, wherein at least the toothed working zone 2 of the rasp is made of plastic material. It is preferred, however, that the connecting part 3 of the rasp is made of plastic as well, so that the entire rasp is made of plastics. The connecting part 3 is adapted to couple the rasp to an impact tool, which generates the working impacts for driving the rasp into (or out of) the bone. Such an impact tool, which is driven pneumatically is e.g. known from the U.S. Pat. No. 5,152,352. Such a tool is especially suited for the driving of rasps made of plastic because the high frequency machine pulses of such impact tools have a small amplitude compared to other impact tools such as hammers or sliding hammers, respectively, and, therefore, overstressing of the bone rasp made of plastic is avoided.

The cleaning of the bone by flush cleaning is of great importance for the success of the operation, not only during the first time implantation of a prosthesis, but especially when a prosthesis which had been fixed with bone cement is to be replaced by a new prosthesis. Remains of old bone cement, connective tissue and bone lamella are scraped free and raked out during the working of the bone with the rasp. The seat in the bone is then prepared by flushing, scavenging and sucking off for receiving the new prosthesis. With the known rasps, this flushing, scavenging and sucking off step is performed using curets or other instruments after the working step, i.e. after removal of the bone rasp. Preferably, the new bone rasp made of plastic is provided with a bore 7, which can be connected to a flushing and sucking off line at the proximal end of the rasp and which is open at the distal end 8 of the rasp. By this feature the rasping, the flushing and the sucking off of cement, bone and spongiosa rests can be performed in one step. At the same time the flushing during the rasping has a cooling function. Such a cooling of the bone is helpful since the driving-in of the rasp can produce heat which may cause heat necrosis of active bone material.

Preferably, the rasp is provided with a working part 2 which has toothing of different inclination. The rasp shown in FIG. 1 has a front and middle working section which are provided with a first toothing 5. The back section of the working zone, where the rasp is getting considerably broader, is provided with a finer toothing 6. A swift and at the same time gentle working of the bone is thus possible.

Figure 2:
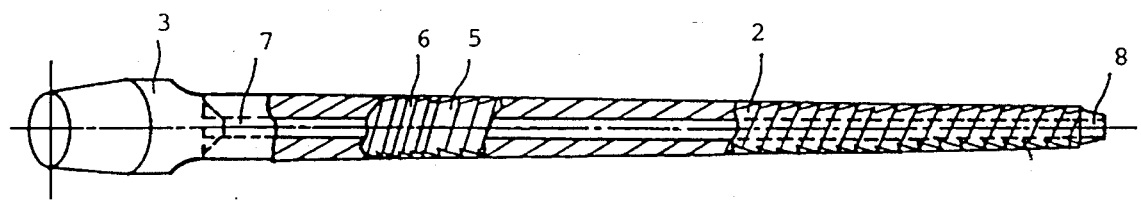
FIG. 2 is a (partly sectional) view of the smaller side of the rasp of FIG. 1.
Figure 3:
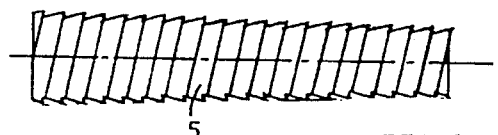
FIG. 3 is a view of the broader side of the middle part of the working zone of the rasp of FIG. 1.
Figure 4:
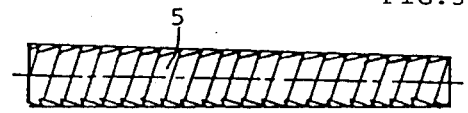
FIG. 4 is a view of the smaller side of the middle part of the working zone of the rasp.
Figure 5:
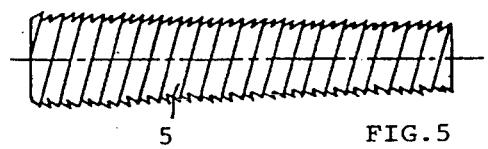
FIG. 5 is a view of the broader side of the middle part of the working zone of a rasp with double toothing.
Figure 6:
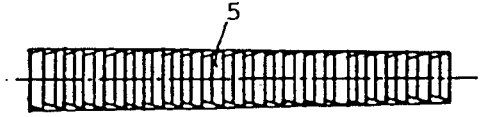
FIG. 6 is a view of the smaller side of the middle of the working zone with double toothing.

FIG. 2 shows the narrow side view of the rasp of FIG. 1, wherein the same reference numerals as in FIG. 1 designate same elements. FIG. 3 and FIG. 4 show the toothing of the middle working section. FIG. 5 and FIG. 6 show another embodiment of the toothing, wherein the narrow side toothing of the rasp is a double toothing.

The plastic material of the rasp can be chosen among various known kinds of plastic types, e.g. from one of the following types: polyoxymethylenes (POM), polyamides (PA), polyethylenes (PE), liquid crystalline polymers (LCP), polyvinylidenfluorides (PVDF). The plastics can be reinforced by the addition of carbon fibers.

The preferred plastic material of the mentioned materials is polyoxymethylene. Another preferred material is polycarbonate, especially the type Macrolon 2805 of the company Bayer AG.

The rasp can be produced by the known methods for forming an article of plastic material, e.g. by injection molding, by hot forming or by machining of a blank, respectively.

While there are shown and described present preferred embodiments of the invention, it is to be distinctly understood that the invention is not limited thereto, but may be otherwise variously embodied and practiced within the scope of the following claims.

We claim:

1. A surgical bone rasp for the surgical working of bone material by oscillating movement of said bone rasp for preparing a bone to receive a prosthesis, said surgical bone rasp comprising:

a toothed, elongate working section having teeth with cutting edges, said teeth extending from a distal end to a proximal end of said working section, and a connecting section arranged at said proximal end for the connection of said bone rasp to an impact tool, wherein said toothed working section including said teeth and cutting edges is made of only plastic or carbon fiber reinforced plastic material, and wherein said toothed, elongate working section is provided with a longitudinally extending bore with a distal and proximal end, said bore being open at the distal end of said working section and being open at the proximal end of said working section, and said connecting section is arranged at an angle to said longitudinal bore at said proximal end of said working section such that the proximal end opening of said bore in said working section is connectable to a flushing and suction line when said connecting section is connected to an impact tool.

2. Bone rasp according to claim 1, wherein said connecting section is made of only plastic material, which plastic material may be a carbon fiber reinforced plastic material.

3. Bone rasp according to claim 1, wherein said working section is provided with zones having each different inclination of said toothing.

4. Bone rasp according to claim 1, wherein said working section is provided with a broad side and a narrow side, said narrow side being provided with a double toothing.

5. Bone rasp according to claim 1, wherein said plastic material is a polycarbonate plastic material.

6. Bone rasp according to claim 1, wherein said plastic material is a polyoxymethylene plastic material.

7. A surgical bone rasp for the surgical working of bone material by oscillating movement of said bone rasp for preparing a bone to receive a prosthesis, said surgical bone rasp comprising:

a toothed, elongate working section having teeth with cutting edges, said teeth extending from a distal end to a proximal end of said working section, and a connecting section arranged at said proximal end for the connection of said bone rasp to an impact tool, wherein said toothed working section including said teeth and cutting edges and said connecting section are made of only plastic or carbon fiber reinforced plastic material, and wherein said toothed, elongate working section is provided with a longitudinally extending bore with a distal and proximal end, said bore being open at the distal end of said working section and being open at the proximal end of said working section, and said connecting section is arranged at an angle to said longitudinal bore at said proximal end of said working section such that the proximal end opening of said bore in said working section is connectable to a flushing and suction line when said connecting section is connected to an impact tool.

8. Bone rasp according to claim 7, wherein said working section is provided with zones having each different inclination of said toothing.

9. Bone rasp according to claim 7, wherein said working section is provided with a broad side and a narrow side said narrow side being provided with a double toothing.

10. Bone rasp according to claim 7, wherein said plastic material is a polycarbonate plastic material.

11. Bone rasp according to claim 7, wherein said plastic material is a polyoxymethylene plastic material.

* * * * *